United States Patent
Rugnone

(10) Patent No.: US 10,781,167 B2
(45) Date of Patent: Sep. 22, 2020

(54) UREA PROCESS WITH HIGH-TEMPERATURE STRIPPING

(71) Applicant: Casale SA, Lugano (CH)

(72) Inventor: Luca Rugnone, Como (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 15/780,086

(22) PCT Filed: Dec. 9, 2016

(86) PCT No.: PCT/EP2016/080443
§ 371 (c)(1),
(2) Date: May 30, 2018

(87) PCT Pub. No.: WO2017/097981
PCT Pub. Date: Jun. 15, 2017

(65) Prior Publication Data
US 2018/0362452 A1    Dec. 20, 2018

(30) Foreign Application Priority Data

Dec. 11, 2015  (EP) .................................... 15199482

(51) Int. Cl.
*C07C 273/04* (2006.01)
*B01D 3/04* (2006.01)
*C07C 273/16* (2006.01)
*B01D 1/06* (2006.01)
*B01D 3/00* (2006.01)

(52) U.S. Cl.
CPC .......... *C07C 273/04* (2013.01); *B01D 1/065* (2013.01); *B01D 3/009* (2013.01); *B01D 3/04* (2013.01); *C07C 273/16* (2013.01); *Y02P 20/127* (2015.11)

(58) Field of Classification Search
CPC .................................................. C07C 273/04
See application file for complete search history.

(56) References Cited

U.S. PATENT DOCUMENTS

| | | |
|---|---|---|
| 3,957,868 A | 5/1976 | Verstegen et al. |
| 4,899,813 A | 2/1990 | Menicatti et al. |
| 2012/0296120 A1 | 11/2012 | Scotto et al. |
| 2014/0081046 A1 | 3/2014 | Carlessi et al. |

FOREIGN PATENT DOCUMENTS

| | | |
|---|---|---|
| RU | 2309947 C1 | 11/2007 |
| SU | 1774623 A1 | 5/1996 |
| UA | 46324 U | 12/2009 |

OTHER PUBLICATIONS

International Search Report dated Mar. 1, 2017 in connection with PCT/EP2016/080443.
International Preliminary Report on Patentability dated Jan. 12, 2018 in connection with PCT/EP2016/080443.
Meessen, Jozef H., "Urea, Ullmann's Encyclopedia of Industrial Chemistry," 2012, Wiley-VCH Verlag GmbH & Co. KGaA, pp. 666, 667, 670 and 671.

*Primary Examiner* — Ana Z Muresan
(74) *Attorney, Agent, or Firm* — Akerman LLP

(57) ABSTRACT

A shell-and-tube stripper for carbamate decomposition and ammonia recovery from a urea solution comprising a bundle of heated tubes, said tubes being fed with said urea solution and carbon dioxide as stripping medium, the urea solutions forming a liquid falling film on the internal surface of the tubes and the carbon dioxide forming a counter-current gaseous flow; said tubes comprise an external layer made of super austenitic or super duplex stainless steel and an internal layer made of zirconium, said internal layer reaching temperatures higher than 220° C.

15 Claims, 4 Drawing Sheets

UREA PROCESS WITH HIGH-TEMPERATURE STRIPPING

This application is a national phase of PCT/EP2016/080443, filed Dec. 9, 2016, and claims priority to EP 15199482.9, filed Dec. 11, 2015, the entire contents of both of which are hereby incorporated by reference.

Field of the Invention

The invention relates to the field of urea production. The invention relates in particular to high-temperature stripping in a process for the urea production.

Prior Art

Urea is synthesized by reacting ammonia and carbon dioxide. A discussion of the various processes and related plants for the urea production can be found in literature, e.g. Ullmann's Encyclopedia of Industrial Chemistry, Wiley-VCH Verlag.

The synthesis of urea involves a fast and highly exothermic step of formation of ammonium carbamate, and a slightly endothermic step of conversion of ammonium carbamate into urea and water. The reaction is carried out in a urea synthesis reactor, which is generally operated at 130-250 bar and 180-200° C.

Due to thermodynamic limitations the conversion to urea is not complete and depends on the composition and operating conditions of the synthesis. The reactor effluent is an aqueous solution of urea containing significant amounts of unconverted ammonium carbamate and ammonia. Typically, conversion of a urea reactor operating at 140 bar and 185° C. is 60-63%, which corresponds to a urea concentration of 30-34% by weight in the reactor effluent, the remainder being essentially formed by water, ammonium carbamate, and ammonia. The urea reactor conversion is intended as the ratio between the moles of carbon converted into urea (i.e. the moles of urea) and the total moles of carbon in the solution (i.e. the converted carbon plus the not converted carbon).

The stripping technology is a known technique to recover the unconverted ammonia and ammonium carbamate and recycle it back to the synthesis reactor. According to this technology, the reactor effluent is subjected, in an appropriate stripper, to a heat treatment for the decomposition of the carbamate into ammonia and carbon dioxide and removal of most of the unconverted ammonia, possibly with the aid of a stripping medium such as carbon dioxide. The stripper contains a bundle of externally heated tubes; the reactor effluent flows in the tube side forming a liquid film on the internal wall of tubes (falling film stripper). The heat source is usually steam.

The stripping process produces a stripped solution and a gaseous phase containing ammonia and carbon dioxide which is collected at the top of the stripper. Said gaseous phase is condensed to carbamate in a high-pressure carbamate condenser and the carbamate is recycled to the synthesis reactor. The stripped solution is sent to a urea recovery section where the unconverted carbamate is further removed and a flow of recycled solution is produced, which is also sent to the high-pressure condenser. The recycled solution contains some extra water which is necessary to allow the condensation of vapours at lower pressure and furthermore to keep the liquid far from the risk of crystallization. This additional water is finally recycled to the urea reactor with negative impact on the conversion and the plant energy consumption.

The stripper is usually part of an isobaric loop together with the synthesis reactor and the condenser, which means that the stripping process is carried out at about the same high pressure as synthesis.

The effluent of the reactor enters the tubes of the stripper at a temperature of about 185° C. The temperature of the liquid film through each tube is typically ascending in a first portion of the tube, reaching a peak value, and descending in a second portion of the tube, the outlet temperature being lower than the inlet temperature, typically in the range 165 to 175° C.

The peak temperature is typically reached at about 30-40% of the length of the tube. In the prior art, the process is designed and operated in such a way that the peak temperature of the film is not greater than 200° C. to avoid corrosion. Consequently, the heat source steam is generally at a pressure not greater than 25 bar.

The stripping process is considered the state-of-the-art technique for urea plants but still has some drawbacks. The conversion of a urea plant is 60-63% at urea reactor outlet while the same is increasing up to about 80% once the solution is passing through the high pressure stripper. This is because the unconverted carbamate is partly removed by the stripper and the concentration of urea out of the total is increasing. This is a significant improvement compared to the non-stripping technology, however a certain amount of unconverted carbamate is still found in the aqueous solution leaving the stripper. Conventionally, said aqueous solution is further treated in at least one other urea recovery unit at a lower pressure and recovered ammonia and carbon dioxide are condensed and pumped back to the high pressure loop. A first drawback is that cost and complication of the plant are increased. A further drawback is that the recycled solution generated in the urea recovery unit contains some water which is finally introduced in the high-pressure loop, and particularly in the reactor, having a negative impact on the thermodynamic and kinetic of the urea synthesis.

SUMMARY OF THE INVENTION

The aim of the invention is to eliminate the above mentioned shortcomings of the prior art.

The above aim is reached with a stripping process of an aqueous urea solution according to claim 1. The aqueous urea solution is a reactor effluent and comprises unconverted ammonium carbamate and ammonia. The stripping of the invention is performed at the same or substantially the same pressure of the reactor (urea synthesis pressure) and in a falling-film shell-and-tube stripper using carbon dioxide as a stripping medium. The process is characterized in that a liquid film of said solution formed in the tubes has a peak temperature of at least 220° C. Preferably, said peak temperature is comprised in the range of 220 to 250° C.

The applicant has found that one reason behind the limited efficiency of the conventional stripping process is that the decomposition temperature of the residual ammonium carbamate in the reactor effluent is above 200° C. at the typical pressure of urea synthesis.

Hence the prior art approach of keeping the peak temperature of the falling film to 200° C. results in the liquid film being significantly below the decomposition temperature in the second portion of the tube generally corresponding to around 60-70% of the total length of the tube.

As a consequence, the unconverted carbamate and ammonia are removed from the liquid film mostly due to the stripping effect of the carbon dioxide used as stripping medium. In particular, carbon dioxide drastically lowers the ammonia partial pressure so as to boost the release of the unconverted carbamate and ammonia from the liquid to the gaseous phase as per the mass transfer effect.

This introduces a strong limitation in the recovery capacity of the stripper, since it is driven by mass transfer for around 60-70% of tube length and by thermal decomposition only for the remaining 30-40% of the total length of the tube.

On the contrary, a peak temperature of 220° C. or above, according to the present invention, results in a drastic and unexpected improvement of carbamate recovery in the high-pressure loop, since the average temperature of the stripping process is kept above the decomposition temperature of carbamate. The invention provides a better conversion of carbon dioxide to urea compared to the prior art. In some embodiments, the invention achieves a conversion at the stripper outlet of 96% or higher compared to 80% of a conventional stripper. Said conversion of at least 96% corresponds to a urea in a concentration of at least 70% by weight.

In preferred embodiments, the stripper effluent contains an amount of unconverted ammonia corresponding to a concentration not greater than 2% by weight, more preferably not greater than 1% by weight, and/or an amount of unconverted ammonium carbamate corresponding to a concentration not greater than 4% by weight, more preferably not greater than 3% by weight.

Taking into account that carbon dioxide has a molecular mass of 44, ammonia has a molecular mass of 17 and ammonium carbamate has a molecular mass of 78, a concentration of unconverted ammonium carbamate of 3-4% by weight could be also intended as a concentration of about 2% by weight of unconverted carbon dioxide plus a concentration of about 1.5% by weight of unconverted ammonia. This is a way to refer the concentration of unconverted ammonium carbamate directly to the reactants, i.e. carbon dioxide and ammonia.

Due to the higher average temperature of the process, the stripping of the invention can be termed "high temperature stripping" and the related apparatus a "high temperature stripper".

The tubes of the high-temperature stripper of the invention are preferably realized with an outer layer of a stainless steel and a heat and corrosion resistant inner layer. Preferably, said inner layer is made of zirconium. More preferably, said outer layer is made of a super austenitic stainless steel (e.g. 25Cr22Ni2Mo) or a super duplex stainless steel (e.g. Safurex, DP28W).

Preferably, said tubes are heated by means of condensing steam at a pressure of at least 30 bar, more preferably in the range of 35 to 50 bar.

Preferably, the liquid falling film along the tubes of the stripper has a first temperature at the tube inlet, said first temperature being in the range 175 to 195° C. and preferably 180 to 185° C.; a peak temperature in an intermediate region of the tube in the range 220 to 250° C. and preferably 240° C.; a second temperature at the tube outlet, said second temperature being 5 to 10° C. greater than said first temperature, preferably 190 to 195° C.

Achieving a higher conversion of carbon dioxide to urea in the high pressure loop, that is a less amount of unconverted carbamate in the effluent, is a great advantage of the invention and reduces the size and cost of a subsequent low-pressure recovery section and the amount of water which is inevitably recycled to the reactor. In some embodiments of the invention, the effluent of the high-pressure stripper is sent directly to a concentration and finishing section, i.e. without any step of carbamate decomposition at a pressure lower than synthesis pressure.

The invention also achieves higher energy efficiency. By reintroducing less water into the reactor, the invention obtains a higher conversion of reactor (i.e. 70% against 60-63% of common reactors) and, consequently, a lower energy consumption of the stripper and globally of the plant if compared to the prior art. Also, the condenser is able to export a greater amount of energy, preferably in the form of steam. The additional steam can be used, for example, to power a steam turbine driver of the carbon dioxide compressor.

Further objects of the invention are stated in the attached claims.

The advantages will emerge even more clearly with the aid of the description below, relating to a preferred embodiment.

DETAILED DESCRIPTION OF PREFERRED EMBODIMENTS

Figure 1:
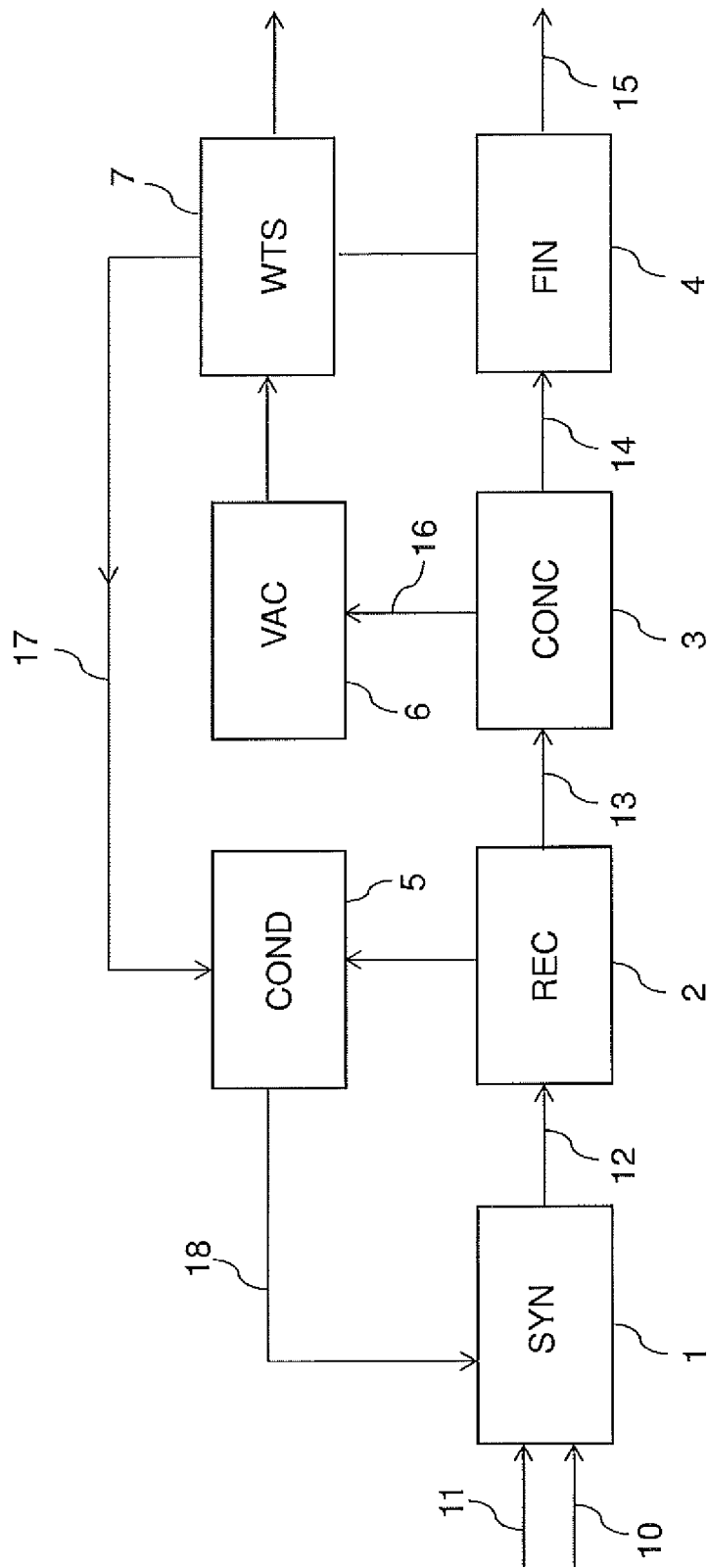
FIG. 1 shows a block scheme of a urea plant according to an embodiment of the invention.

FIG. 1 illustrates a block scheme of a urea plant according to a first embodiment of the invention.

The urea plant comprises basically: a high-pressure synthesis section (SYN) 1, a recovery section (REC) 2, a vacuum concentration section (CONC) 3, a finishing section (FIN) 4, a condensation and recycle section (COND) 5, a vacuum condensation unit (VAC) 6 and a waste water treatment section (WTS) 7.

Ammonia feed 10 and carbon dioxide feed 11 are reacted in the synthesis section 1 to produce an aqueous solution 12 of urea; said solution 12 is further treated in the recovery section 2 which comprises at least one decomposition unit where unconverted carbamate contained in the solution 12 is decomposed to ammonia and carbon dioxide.

The output of said section 2 is an aqueous solution 13 which is sent to the vacuum concentration unit 3 where water is removed until a desired concentration is reached, suitable for finishing in the subsequent section 4.

The stream 14 delivered by said unit 3 for example may be a solution of 95% or more urea, which is suitable for granulation, or a urea melt having a purity of 99.7% or more which is suitable for prilling. Urea 15 in a solid form is produced in the section 4.

Water removed from the solution 13 is sent via line 16 to the condensation unit 6 and waste water treatment section 7. The stream 16 is still contaminated with some ammonia and carbon dioxide, which are recycled to the synthesis section 1 via line 17, through the condensation and recycle section 5 and carbamate recycle line 18.

Figure 2:
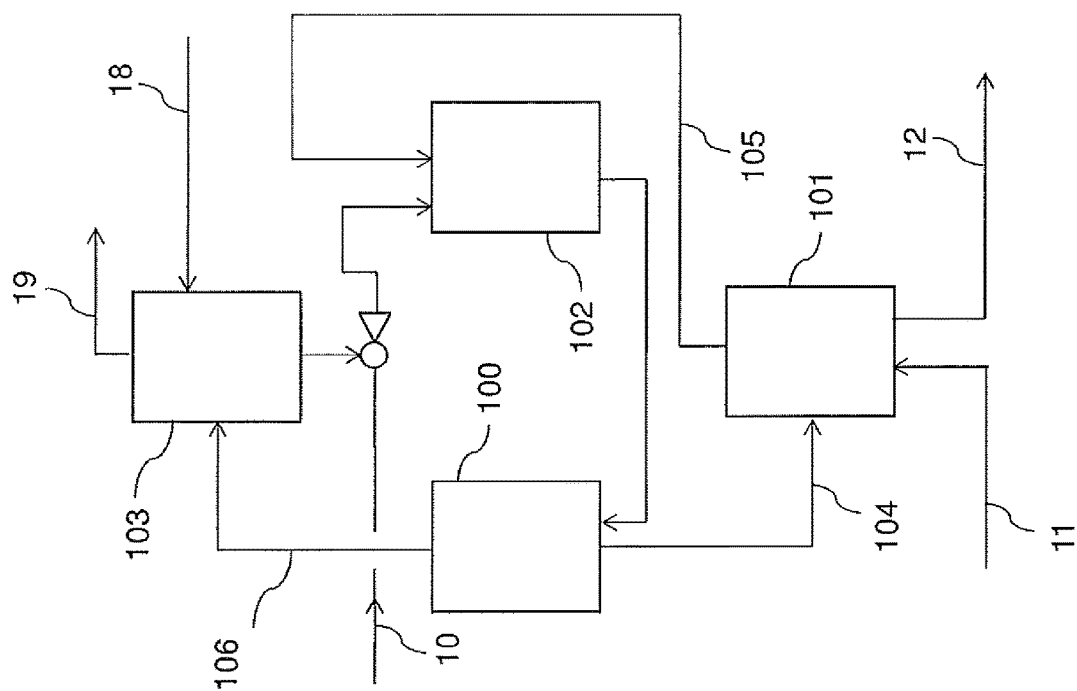
FIG. 2 is a first embodiment of the high-pressure synthesis loop of the plant of FIG. 1.

As illustrated in FIG. 2, the synthesis section 1 includes a reactor 100, a stripper 101, a condenser 102 and a scrubber 103.

The effluent 104 of the reactor 100 is sent to the stripper 101 which produces the solution 12; overhead gas 105 of the stripper, which is predominantly ammonia and carbon dioxide, is condensed in the condenser 102 and recycled to the reactor 100.

The overhead gas 106 of the reactor 100 is scrubbed in the scrubber 103, which is also supplied with the carbamate recycle 18, to separate inert gas 19; the carbamate solution from the scrubber is sent to the reactor, together with the ammonia feed 10, via the condenser 102.

Figure 3:
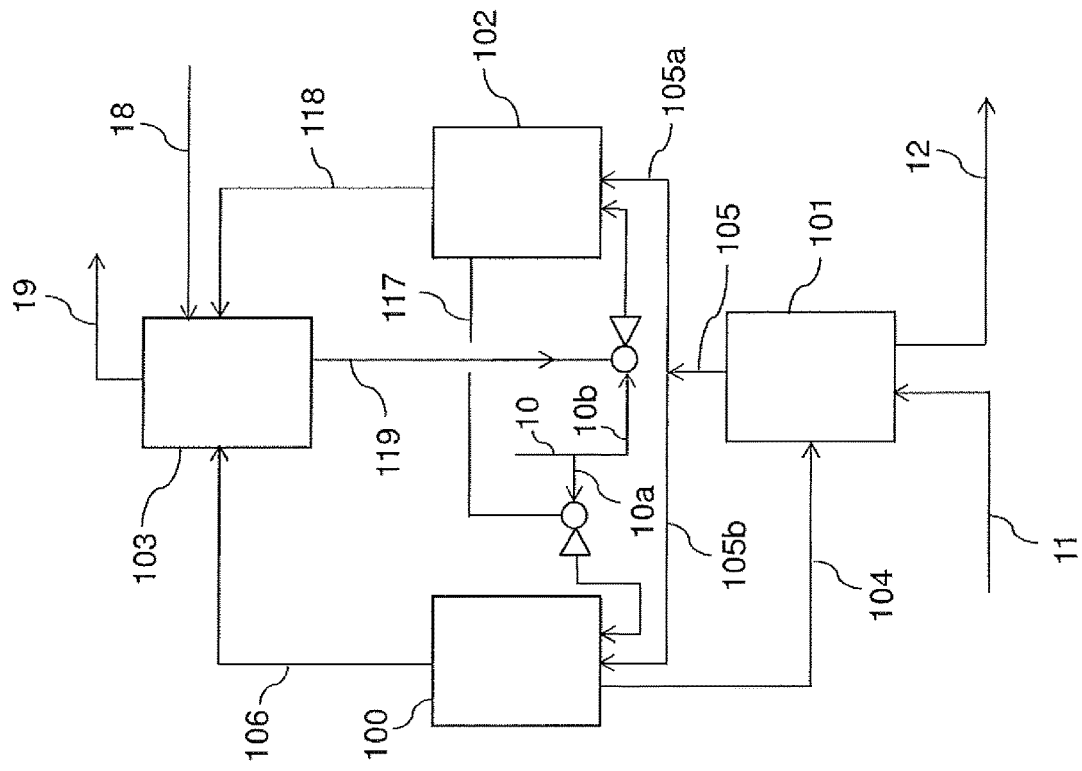
FIG. 3 is another embodiment of the high-pressure synthesis loop of the plant of FIG. 1.

The inert gas 19 from the scrubber 103 can be purged to the atmosphere or better can be further treated in a washing column prior to the discharge, FIG. 3 illustrates a scheme of the synthesis section 1 according to the Split-Flow-Loop™ technology and the Full-Condenser™ technology.

A portion 10a of the ammonia feed is sent to the reactor 100 and a portion 10b is sent to the condenser 102.

The effluent 104 of the reactor 100 is sent to the stripper 101 together with carbon dioxide 11, producing the solution 12 and the gas 105 predominantly containing ammonia and carbon dioxide.

A first portion 105a of the overhead gas of the stripper 101 is sent to the condenser 102, while a second portion 105b is sent to the reactor 100. Preferably, said first portion 105a is about two thirds of the total gas 105 coming from the stripper and the second portion 105b is the remaining one thirds.

Said first portion 105a is at least partially condensed to carbamate 117, and feeds the reactor 100 together with ammonia 10a. The remaining non-condensed vapours 118, which contain some inert gases, are sent the scrubber 103 together with the inert gases they contain. Said non-condensed vapours 118 are a small amount with respect to the condensate 117.

The overhead gas 106 of the reactor 100 is scrubbed in the scrubber 103 to separate inert gases 19 contained therein and provide a carbamate solution 119. Said carbamate solution 119 is sent to the condenser 102 together with the ammonia feed 10b and said inert gases 19 are purged to the atmosphere or further treated in a washing column prior to the discharge.

Figure 4:
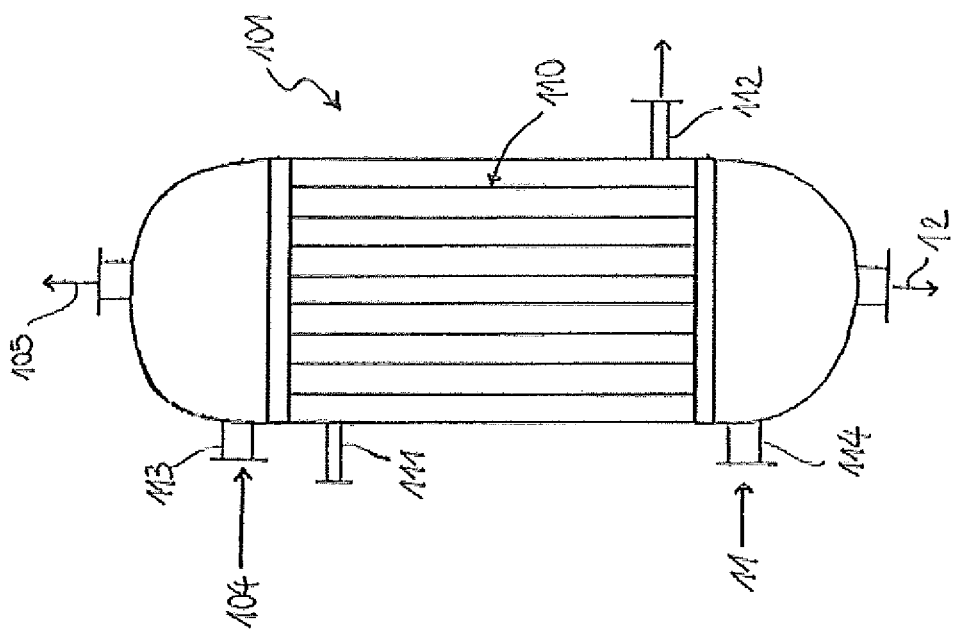
FIG. 4 is a schematic illustration of the stripper of the synthesis loop of FIG. 2 or 3.

FIG. 4 illustrates a preferred embodiment of the stripper 101 (high-temperature stripper). The stripper 101 is a steam-heated tube-bundle equipment including a bundle of tubes 110 externally heated by steam entering at steam inlet 111 and leaving at steam or condensate outlet 112. The reactor effluent 104 is fed to the inlet of tubes 110 (tube side) via inlet 113 and suitable distribution means. Carbon dioxide 11 is also fed to the tubes via carbon dioxide inlet 114 to act as a stripping agent. Inside the tubes, the aqueous solution 104 forms a liquid film which is contacted with the rising gaseous stream of carbon dioxide 11, providing the stripped solution 12 and the overhead gas 105.

Figure 5:
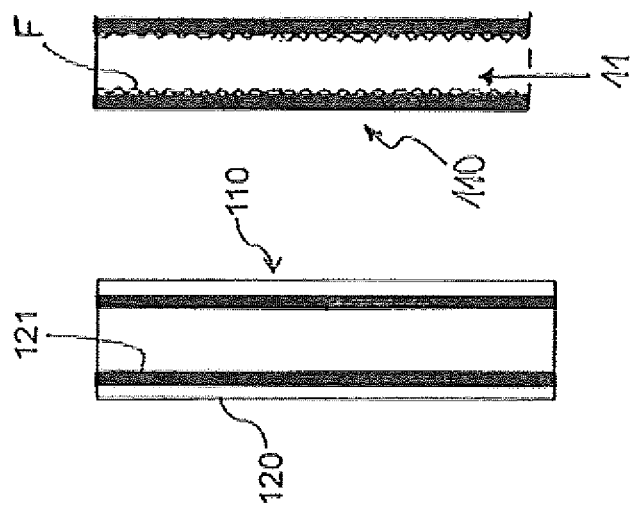
FIG. 5 represents a cross-section of a tube of the stripper of FIG. 4.

FIG. 5 shows a preferred embodiment of tubes 110. Each tube 110 is preferably a bimetallic tube including an outer layer 120 made of a suitable stainless steel and an inner layer or inner coating 121 made of zirconium. Preferably each tube 110 has an inner diameter of around 25 mm and a thickness of around 3 mm.

Figure 6:
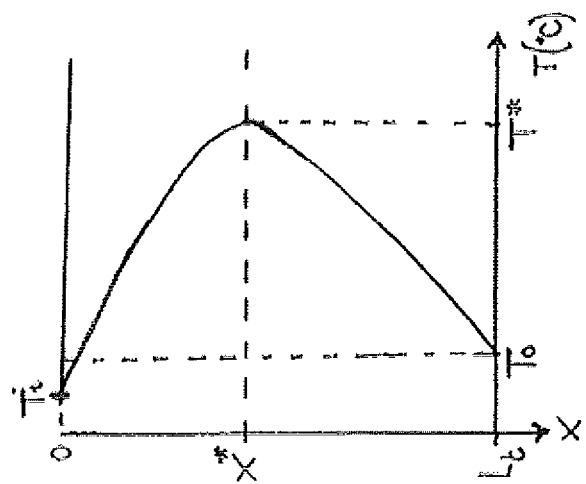
FIG. 6 illustrates a thermal profile of the liquid film flowing inside the tube of FIG. 5.

FIG. 6 shows a temperature profile of the liquid film F flowing inside a tube 110. The temperature is pictured as a function of a coordinate x along the axis of the tube 110. The origin of the coordinate x is assumed at the liquid inlet, i.e. upper end of the tube 110.

The liquid film F has an inlet tube temperature Ti at coordinate x=0 which is for example 185° C. and an outlet tube temperature To at coordinate x=Lt where Lt is the length of the tube. The outlet temperature To is slightly greater than said inlet temperature, for example 190° C. The temperature T is ascending in a first portion of tube 110, namely from coordinate x=0 to x* and then descending from x* to L. The peak temperature T* measured at coordinate x* is above 220° C., for example 240° C. in the shown example. The temperature drop in the second portion of the tube (x* to Lt) is due to the cooling effect of the fresh carbon dioxide 11. The evaporation of ammonia and some ammonium carbamate due to mass transfer removes some enthalpy from the liquid phase and, as a consequence, the temperature decreases.

It can be noted that the temperature of the film is above 200° C. along a substantial portion of the tube 110. As a consequence, most of the unconverted carbamate contained in the effluent 104 is dissociated and the output solution 12 has a reduced amount of residual carbamate if compared to the prior art.

Looking at FIG. 1, it shall be noted that the invention reduces drastically the flow rate of condensate 18 compared to a prior art process using a conventional stripper. The condensate flow 18 contains water which is detrimental to the synthesis of urea; then the invention allows improve the conversion yield in the synthesis section 1.

Figure 7:
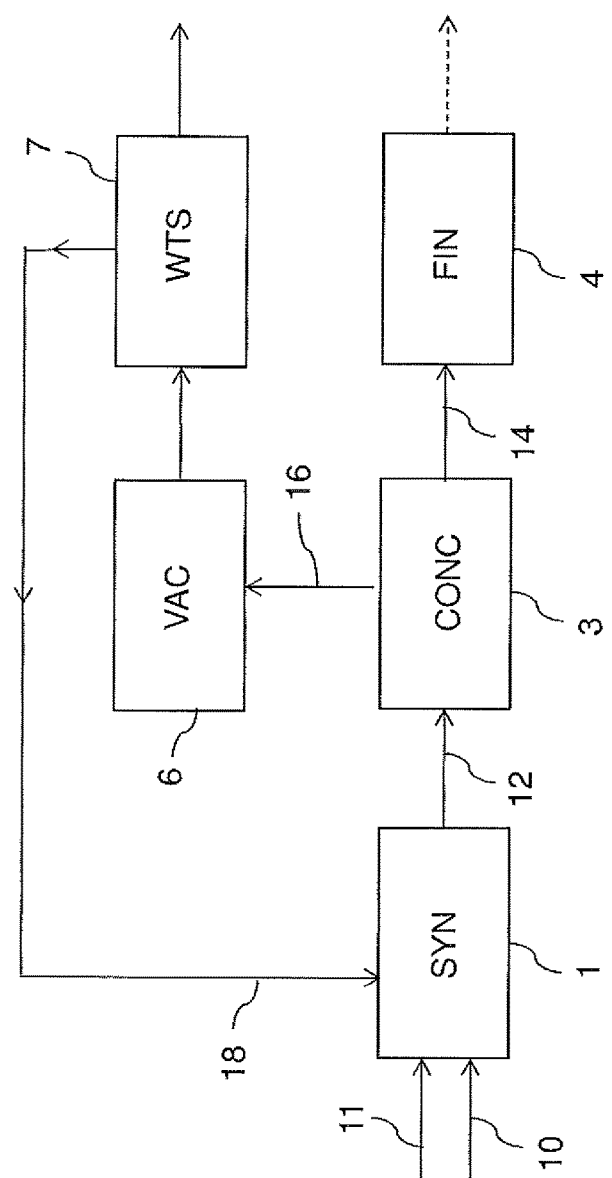
FIG. 7 is a scheme of a urea plant according to another embodiment of the invention.

FIG. 7 is a further embodiment of the invention which is a variant of FIG. 1 where the effluent 12 is directly sent to the vacuum concentration section 3, that is without the need of recovery section 2. This results in a drastic simplification of the plant and reduction of the related cost. The embodiment of FIG. 7 is made possible by the inventive stripper which is able to deliver a solution 12 containing only 1-2% of residual carbamate. Such a solution can be admitted directly to the vacuum concentration section 3.

For example the stream 12 may have a pressure of 140 bar, a temperature around 190° C. and the following composition (% weight): Urea 70%; water 25%; ammonia not greater than 1-2%; ammonium carbamate not greater than 3-4%.

Figure 8:
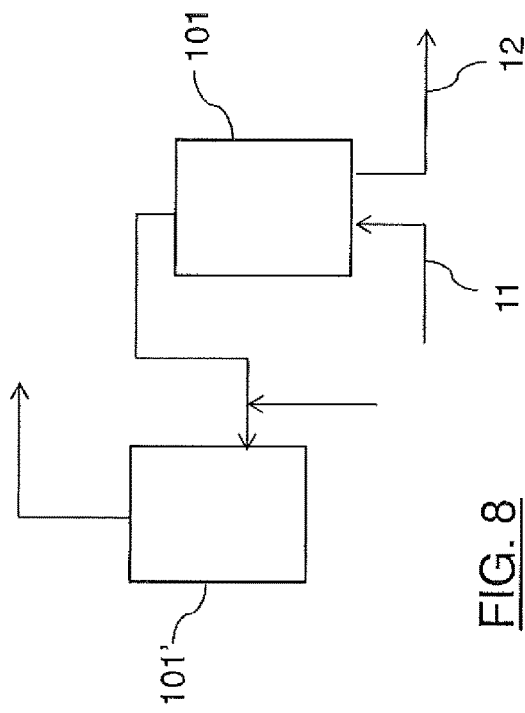
FIG. 8 is a scheme of the high-pressure synthesis loop of the plant of FIG. 7.

FIG. 8 illustrates a high pressure synthesis loop of the plant of FIG. 7 where the reactor 100 and the condenser 102 are integrated in a single equipment 101'. This solution further contributes to reduce the plant cost and to simplify the scheme of the plant.

The invention can be applied also to revamping of existing urea plants. A method for revamping a urea plant may include replacing an existing stripper with a stripper according to the invention. In some embodiments, recovery section can be bypassed thanks to the lower content of unconverted carbamate delivered by the new stripper.

For example, a urea plant for the synthesis of urea comprising a high-pressure synthesis loop with a conventional stripper, a recovery section and a vacuum concentration unit, can be revamped by: replacing the stripper with a stripper according to the invention and providing a line to feed the effluent of the newly-installed stripper directly to the vacuum concentration unit.

What is claimed is:

1. A process of stripping of an aqueous urea solution comprising unconverted carbamate ammonium and ammonia, wherein said solution is contacted with gaseous carbon dioxide acting as a stripping medium, and the stripping takes place at a synthesis pressure of said solution,
wherein the process of stripping of the aqueous urea solution is performed in a falling-film shell-and-tube stripper, wherein a liquid film of said solution formed in the tubes of said stripper has a peak temperature of at least 220° C.

2. The process according to claim 1, said peak temperature being in the range 220 to 250° C.

3. The process according to claim 1, wherein the tubes of said stripper include an outer layer of a stainless steel and a heat and corrosion resistant inner layer.

4. The process according to claim 3, said outer layer being of a super austenitic stainless steel or a super duplex stainless steel.

5. The process according to claim 3, said heat and corrosion resistant inner layer being made of zirconium.

6. The process according to claim 1, wherein said tubes are heated by a condensing steam at a pressure of at least 30 bar.

7. The process according to claim 1, further comprising providing a stripped solution comprising urea in a concentration of at least 70% by weight.

8. The process according to claim 1, further comprising providing a stripped solution containing an amount of unconverted ammonia corresponding to a concentration not greater than 2% by weight and/or an amount of unconverted ammonium carbamate corresponding to a concentration not greater than 4% by weight.

9. The process according to claim 1, said liquid film having:
a first temperature at the tube inlet, said first temperature being in the range 175 to 195° C.;
a peak temperature in an intermediate region of the tube in the range 220 to 250° C.;
a second temperature at the tube outlet, said second temperature being 5 to 10° C. greater than said first temperature.

10. A process for the synthesis of urea from ammonia and carbon dioxide, including the formation of an aqueous urea solution at a synthesis pressure, said solution comprising unconverted ammonium carbamate and ammonia, and further including a stripping of said solution with gaseous carbon dioxide as a stripping medium and at said synthesis pressure, said stripping being performed in a falling-film shell-and-tube stripper and producing a stream of a stripped solution,
wherein during the stripping process a liquid film of said solution formed in the tubes of said stripper has a peak temperature of at least 220° C.

11. The process according to claim 10, wherein said stripped solution has a urea concentration of at least 70% by weight and/or contains an amount of unconverted ammonia corresponding to a concentration of not greater than 2% by weight, and/or an amount of unconverted ammonium carbamate corresponding to a concentration not greater than 4% by weight.

12. The process according to claim 11, wherein at least part of said stripped solution is sent directly to a vacuum concentration section.

13. The process according to claim 8, wherein the stripped solution contains an amount of unconverted ammonia corresponding to a concentration not greater than 1% by weight and/or an amount of unconverted ammonium carbamate corresponding to a concentration not greater than 3% by weight.

14. The process according to claim 9, wherein said first temperature being in the range 180 to 185° C., and/or said peak temperature being 240° C., and/or said second temperature being in the range 190 to 195° C.

15. The process according to claim 11, wherein said stripped solution contains an amount of unconverted ammonia corresponding to a concentration not greater than 1% by weight and/or an amount of unconverted ammonium carbamate corresponding to a concentration not greater than 3% by weight.

* * * * *